United States Patent [19]
Pierfitte

[11] Patent Number: 5,278,416
[45] Date of Patent: Jan. 11, 1994

[54] TOMOGRAPHIC GAMMA CAMERA PROVIDED WITH A SWIVELLING DETECTOR

[75] Inventor: Michel Pierfitte, Villepreux, France

[73] Assignee: Sopha Medical, Paris, France

[21] Appl. No.: 894,023

[22] Filed: Jun. 4, 1992

[30] Foreign Application Priority Data

Jun. 7, 1991 [FR] France .................. 91-06960

[51] Int. Cl.$^5$ .................................... G01T 1/166
[52] U.S. Cl. ......................... 250/363.05; 250/363.08
[58] Field of Search ................ 250/363.05, 363.08, 250/363.04

[56] References Cited

U.S. PATENT DOCUMENTS

| | | | |
|---|---|---|---|
| 4,220,861 | 9/1980 | Colombo et al. | 250/363.05 |
| 4,652,759 | 3/1987 | Platz. | |
| 4,774,411 | 9/1988 | Span | 250/363.05 |
| 5,105,086 | 4/1992 | Pierfitte et al. | 250/363.08 |
| 5,146,094 | 9/1992 | Stark | 250/363.05 |

FOREIGN PATENT DOCUMENTS 0266846 5/1988 European Pat. Off. .
60-128383 7/1985 Japan .

Primary Examiner—Carolyn E. Fields
Assistant Examiner—Drew A. Dunn

[57] ABSTRACT

The disclosure relates to devices for medical imaging by gamma rays. In a device where a gamma camera is suspended from a supporting frame by a rotating stand, an arm and two pins enabling two movements of rotation of the detector head of the gamma camera with respect to the rotating stand, there is provided a stirrup connected to the arm by a third pin enabling a third rotational movement about this gamma camera. It makes it possible to facilitate the relative movement of the gamma camera and of the patient undergoing the examination.

5 Claims, 1 Drawing Sheet

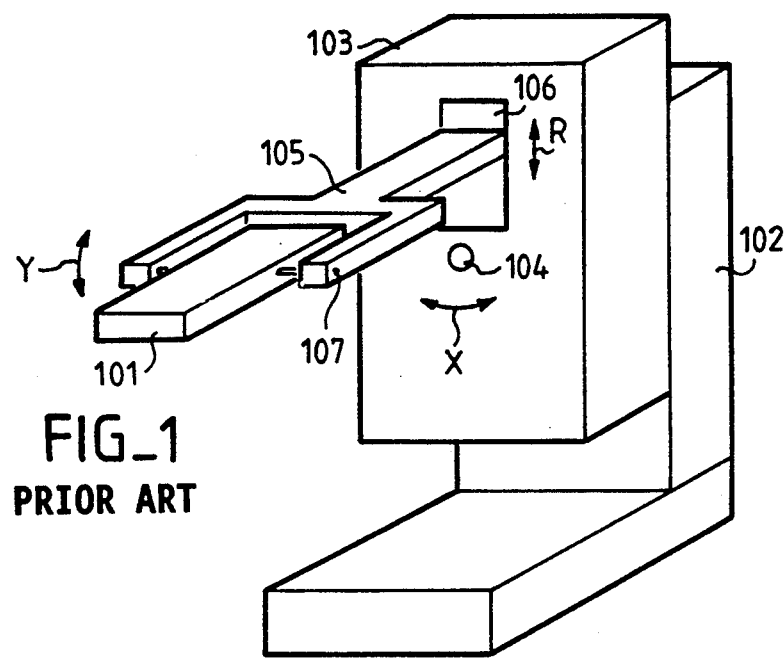
FIG_1
PRIOR ART
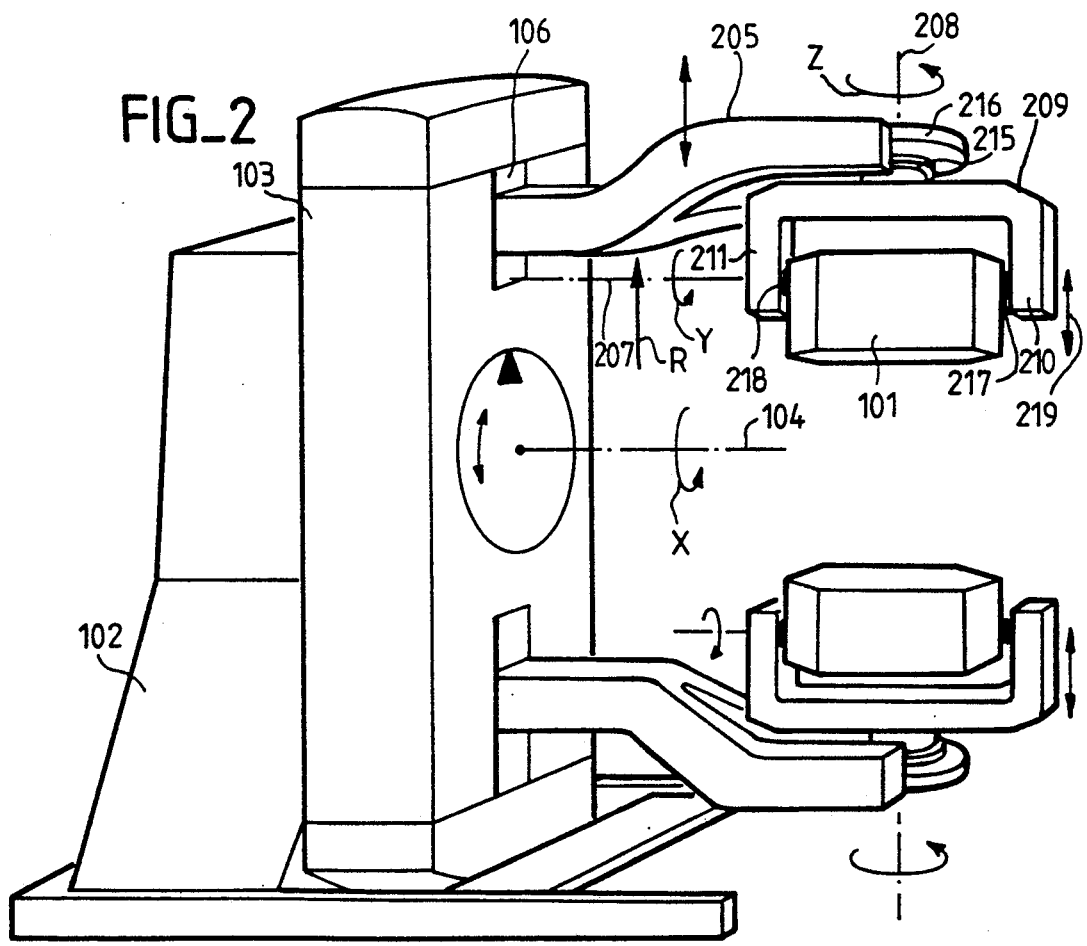
FIG_2

TOMOGRAPHIC GAMMA CAMERA PROVIDED WITH A SWIVELLING DETECTOR

BACKGROUND OF THE INVENTION

1. Field of the Invention

The present invention relates to devices that enable the directional swivelling or orienting of a detector head of a gamma camera, preferably a tomographic gamma camera, appropriately in relation to the patient undergoing an examination with this gamma camera.

2. Description of the Prior Art

Gamma cameras are described, for example, in the U.S. Pat. No. 3,011,057 by Anger. A gamma camera is an apparatus comprising a rotating stand, which is fixed or movable with respect to the ground and carries a detector, also called a detector head, at the end of the arm. This detector is provided with an array of photomultiplier tubes, the input faces of which are juxtaposed with one another and constitute the detection surface of the detector head and its detection field.

The following is the principle of the examination. A radioactive substance is injected into a patient to be examined. This substance is thallium for example. The radioactive emission excites a scintillator crystal of the detector which converts the energy of the gamma photons into a light energy that can be detected by the photomultiplier tubes. The scintillator crystal is preceded, in a standard way, by a collimator defining a sighting direction and characterized by a focal point. This focal point is pushed back to infinity in the case of collimators with parallel, straight or inclined holes. The focal point is at a finite distance, which is positive or negative, in the case of convergent or divergent collimators. The focus is off-centered with respect to a central sighting direction.

The scintillations emitted are detected by the photomultiplier tubes which produce electrical signals depending on the light intensity received. By carrying out barycentric tracking operations on all these electrical signals, it is possible, in a known way, to determine the localization X Y of the origin of the scintillation in the detection field. An incremental acquisition is then carried out by totalizing the number of scintillations (or strokes) detected per localization element called a pixel.

By leaving the detector head in a given position for a certain time above the examined body, it is then possible, for a given angle of sight, called a projection, to obtain an image that reveals the concentration of the emitting substance in the body. The tomographic examination consists in acquiring one image per angle of sight, for a large number of angles of sight, evenly spaced out on an angular sector of at least 180°. It is then possible, with computation algorithms, notably filtered back projection, to reconstitute the image of a volume of the body.

The patient being examined is stretched out on a bed. The bed can be moved directionally with respect to a supporting frame that is fixed, or movable in translation, which supports the gamma camera by means of hinged elements. By combining these different means, it is thus possible to swivel the gamma camera directionally with respect to the patient's body to obtain the desired image of the organ. For obvious reasons of cost, it is necessary to limit, as far as possible, the number of hinges of the elements that support the gamma camera, within the limits of the results to be obtained.

Until recently, the sensitive part of the gamma camera was round. This meant that, all things being equal, the orientation of the patient around the normal to this sensitive part was irrelevant. The instrument used now is a gamma camera with a detector head that has no symmetry of revolution. Its shape may be rectangular, with corners that may or may not be truncated or that may even be elliptical. It is characterized by a big axis and a small axis, which are axes of symmetry in the plane of the detector. The dimension of the big axis is greater than that of the small axis. In these cases, the orientation of the patient about this normal is no longer irrelevant to the most efficient use of the detection field. This requirement further complicates the hinges that have to be provided for.

For the most efficient orientation of the field of detection of the gamma camera, the invention proposes a pin for the directional swivelling of the detector head. This directional swivelling pin is perpendicular to the field of detection of this head. It enables the small axis of this head to be oriented along the axis of the patient, whether the patient is placed in the rotation axis of the stand of the gamma camera or perpendicularly to this rotation axis of the stand.

SUMMARY OF THE INVENTION

An object of the invention, therefore, is a gamma camera of the type comprising a supporting frame, a rotating stand connected to this supporting frame by a rotation axis enabling a rotation of the rotating stand about this ais, one arm connected to the rotating stand by means enabling a radial movement of the arm in a main direction of the rotating stand, a gamma camera detector head held by this arm, a directional swivelling axis enabling this head to be oriented with respect to the arm, wherein this swivelling axis is perpendicular to the rotation pin.

When the gamma camera has an "angulation" axis enabling an angular rotation or "angulation," as defined hereinafter by convention, to be given to the detector head, the swivelling axis is perpendicular to the rotation axis and to the angulation axis, and it connects a stirrup to the end of the arm, this stirrup enabling the head to be oriented with respect to the arm.

BRIEF DESCRIPTION OF THE DRAWINGS

Other special features and advantages of the invention shall appear clearly from the following description, given by way of a non-restrictive example and made with reference to the appended drawings, of which:

FIG. 1 shows an angulation device partially representing the prior art; and

FIG. 2 shows a device according to the invention, limited to the novel means of the invention.

MORE DETAILED DESCRIPTION

The present invention is filed as a patent application at the same time as two other inventions by the same inventor, relating to other improvements.

In the device according to the prior art shown in FIG. 1, a detector head 101 of a gamma camera is held so as to undergo an angulation on an L-shaped supporting frame 102 which lies on the ground. A rotating stand 103 is fixed to the vertical arm of the L by a horizontal pin 104 which enables the rotating stand to carry out a rotational movement X about this axis. By convention, this movement is called a rotation of the gamma camera.

A fork-shaped arm 105 is fixed on the sleeve side to the rotating stand 103 inside a window 106. A known mechanism (not shown) can be used to subject this arm to a radial translation movement R along the rotating stand inside the window so as to move it away from or towards the pin 104.

The detector head 101 of the gamma camera, which is rectangular, is fixed between the two "prongs" of the fork to a pin 107, which is orthogonal to the pin 104 and is horizontal when the rotating stand is vertical (the translation R is then vertical). This axis makes it possible to subject the detector head to a rotational movement Y called an "angulation" by convention.

The patient lies on a bed which is placed beneath the detector head, in parallel or perpendicularly to the pin 104 depending on the needs of the examination. The pin 104 is itself oriented by translation R, rotation X and angulation Y depending on these needs.

The different combinations of these various arrangements and movements are limited. Thus, a situation sometimes arises wherein the large dimension of the gamma camera goes beyond the patient's body in leaving a zone unused or, on the contrary, the smallest dimension of this gamma camera is smaller than the part of the body to be examined. Among other drawbacks, this situation lengthens the duration of the examination, which is painful for the patient, and lowers the productivity of the instrument system.

The device according to the present invention, which enables this problem to be resolved, is shown in FIG. 2 in a manner limited to the specific and novel means of the invention. More particularly, an arm 205 is fixed by one side to the rotating stand movably to obtain the translation movement R, as in FIG. 1. At its other end, this arm bears a pin 208 which is parallel to the radial translation R, and is vertical when the rotating stand is vertical (the translation R is then vertical). This radial translation takes place in a main direction of the stand 103. This pin 208 is perpendicular to the pin 104. It bears a U-shaped stirrup 209, the two lateral sides 210 and 211 of which are parallel to it (they are vertical when the rotating stand is vertical). This pin 208 enables the stirrup, and hence the detector head fixed to it, to be subjected to a rotational movement Z, called a directional swivelling movement by convention.

The detector head 101 of the gamma camera is fixed to the interior of the stirrup 209, between the two flanks of the U, by a pin 207 which is perpendicular to the pin 208. This pin 207 is therefore horizontal when the rotating stand is vertical, and it enables the head to be subjected to the angulation movement Y defined here above with reference to FIG. 1. In order to obtain sufficient clearance without excessively lengthening the lateral arms of the stirrup, the gamma camera is preferably fixed in such a way that its biggest dimension, its big axis, is parallel to the pin 207.

Under these conditions, it is observed that this big dimension of the head of the gamma camera, as shown in FIG. 2, takes the form of the one shown in FIG. 1. To obtain a 90° arrangement, it is enough to make the stirrup rotate about the pin 208 by an angle of 90 degrees, i.e. to make it swivel by 90 degrees in a standard way.

In this way, therefore, the pin 208 makes it possible to give the gamma camera an additional degree of freedom in directional swivelling, to obtain improved relative positioning between itself and the patient undergoing the examination.

The above description has been made with respect to the case where there is only one detector head fixed to the rotating stand by the means described. Its scope naturally extends to the case where the device uses two detector heads fixed to both ends of the rotating stand and hence placed on either side of the patient (one above and the other below when the rotating stand is vertical) as suggested in FIG. 2.

The two heads are held at the end of their arms in the same way. For example, the head 101 is provided with two pins 217 and 218 which may rotate in bearings while holding the head. These bearings are themselves held in flanks, 210 and 211 respectively, of the stirrup 209. The tip of the stirrup 209 is connected to a ring 215 which can rotate inside a concentric ring 216 which is itself fixed to the end of the arm 205.

The stirrup 209, which is shaped like an inverted U, comprises a sliding saddle in each of its flanks 210 and 211 to enable the bearings, which hold the pins 217 and 218, to move vertically. This sliding movement is preferably motor-driven by a motor placed in each stirrup. The motors are independent. One motor is placed, for example, in the center of the stirrup 209. By means of two belts passing through the tip of the stirrup, it drives two worm screws parallel to the flanks 210 and 211. One worm screw is screwed into a nut fixedly joined to a saddle. The saddles are provided with two sleeves which slide along two shafts. The shafts are fixedly joined to the flanks of the stirrup. The head of the worm screw is kept fixed in translation but free in rotation in the stirrup. The telescopic movement is represented symbolically by the double-headed arrow 219 in FIG. 2.

In a simplified version, the angulation movement is manual, with the possibility of selection from among predetermined positions. In one example, these predetermined positions are constituted by notches made on the periphery of circular plates concentric to the angulation pin and fixedly joined to each of the heads. Two catches may get engaged in each of these notches, and thus maintain the angulation of the heads in predetermined positions.

The stirrup may assume any positions in directional swivelling: thus, the tip of the stirrup 209 is connected to a ring 215 which may rotate inside a concentric ring 216 which is itself fixed to the end of the arm 205. The profiles of the rings 215 and 216 are intertwined so as to cause the head to be held in all the positions. When the ring 215 rotates inside the ring 216, the head rotates by a directional swivelling movement about the pin 208. Certain positions in directional swivelling are also preferably pre-defined: for example, the profiles of the rings 215 and 216 may comprises bosses and, respectively, cavities that are evenly spaced out on their circumference which, when they meet each other, get engaged with each other by elastic reaction. This engaging is sufficient to hold the system in its orientation; when forced to do so, the engaging may lead to swivelling to another direction. The directional swivelling may also be motor-driven and, in this case, the motor itself provides for holding the system in its orientation.

What is claimed is:

1. A gamma camera of the type comprising a supporting frame, a rotatable stand connected to this supporting frame by a rotation axis enabling a rotation of the rotatable stand about this axis, one arm connected to the rotatable stand by means enabling a radial movement of the arm perpendicularly to this rotation, a gamma camera detector head held by this arm, wherein said camera further comprises a directional swivelling pin, defining a directional swiveling axis, in the system for holding the detector head, said directional swivelling pin being perpendicular to the rotation axis and enabling said detector head to be oriented with respect to the arm, and an angulation axis making it possible, for a given position in orientation, to provide an angulation of this detector head in a plane perpendicular to the rotation axis.

2. A gamma camera according to claim 1, wherein the detector head is held on the arm by a stirrup to which the detector head is connected by the angulation axis, the directional swivelling axis being perpendicular to the rotation axis and to the angulation axis.

3. A device according to claim I or claim 2, wherein the detector head is fixed to the arm by a U-shaped stirrup within which it is placed, and wherein the directional swivelling axis is fixed to the stirrup substantially at the center of the transversal arm of this U.

4. A device according to any of the claims 1 or 2, wherein the detector head is rectangular and wherein its biggest dimension is parallel to the angulation axis.

5. A device according to any of the claims 1 or 2, further comprising a second assembly formed by an arm, a stirrup, a detector head and two axes, this second assembly being fixed to the rotatable base on the other side of the rotation axis, symmetrically with respect to homologous elements forming a first assembly.

* * * * *